United States Patent [19]

Koyata

[11] 4,349,032
[45] Sep. 14, 1982

[54] ENDOSCOPE WITH AN ULTRASONIC PROBE

[75] Inventor: Kenzi Koyata, Hachioji, Japan

[73] Assignee: Olympus Optical Co., Ltd., Tokyo, Japan

[21] Appl. No.: 101,244

[22] Filed: Dec. 7, 1979

[30] Foreign Application Priority Data

Dec. 15, 1978 [JP] Japan .............................. 53-154657

[51] Int. Cl.³ .............................................. A61B 10/00
[52] U.S. Cl. ...................................... 128/660; 128/4; 73/644
[58] Field of Search ................... 128/660–663, 128/4–9; 358/98; 73/344; 310/328, 336

[56] References Cited

U.S. PATENT DOCUMENTS

| | | | |
|---|---|---|---|
| 3,938,502 | 2/1976 | Bom | 128/661 |
| 3,942,530 | 3/1976 | Northered | 128/4 |
| 3,960,143 | 6/1976 | Terada | 128/4 |
| 4,074,306 | 2/1978 | Kakemuro et al. | 128/6 |
| 4,217,516 | 8/1980 | Iimuma et al. | 128/660 |

FOREIGN PATENT DOCUMENTS 2305501  8/1974  Fed. Rep. of Germany ...... 128/660

OTHER PUBLICATIONS

Ikukoshi, Y., "Apparatus for Endoscopic and UTS Medical Diagnosis", Jap. Unpubl. Pat. Appln. P. Sho 54/1984, Publ. 1/9/79.
Lutz, H. et al., "Transgastroscopic Ultrasonography", Endoscopy, vol. 8, (1976), pp. 203–205.
Hisanaga, K. et al., "A New Trans-Digestive Tract Scanner with a Gastro-Fiber Scope", Proc. 23rd Meeting of AIUM, 1978.

Primary Examiner—Robert W. Michell
Assistant Examiner—Francis J. Jaworski

[57] ABSTRACT

An endoscope has a flexible tube and a bendable tube connected to one end of the flexible tube in which an image guide is inserted and a control section connected to the other end of the flexible tube and having an eyepiece section connected to one end of the image guide to permit observation of a region of interest of a human being and a knob for operating the bendable tube to permit it to be bent. A distal end section of the endoscope is connected to the other end of the bendable tube and has a viewing window connected through an optical system to the other end of the image guide. One ultrasonic probe is provided in proximity to the viewing window and has a directionality in a direction substantially the same as that of an optical axis of the viewing window.

6 Claims, 8 Drawing Figures

ENDOSCOPE WITH AN ULTRASONIC PROBE

BACKGROUND OF THE INVENTION

This invention relates to an endoscope for ultrasonically diagnosing a live tissue, such as a pancreas, located deep in the body of a human being.

Recently, an ultrasonically diagnosing method has been widely accepted in the art. In such ultrasonic diagnosis an ultrasonic pulse is emitted from an ultrasonic probe consisting of an ultrasonic vibration member into a live human tissue. The emitted ultrasonic pulse is partially echoed, while propagated through the live tissue, back to the ultrasonic probe from a boundary between two live parts, such as the bone and pancreas, which have a different acoustic impedance. Such echoes are received by the ultrasonic probe and displayed as a visible image on a cathode ray tube (CRT) after being converted to, for example, a television signal. That is, a tomographic image corresponding to the live tissue is displayed on the CRT. The tissue of cancer, if present in the body, can be found out through utilization of the above-mentioned principle.

In the conventional method, the presence or absence of an abnormal tissue in the body is detected by propagating an ultrasonic wave through the body with an ultrasonic probe in contact with the outer surface or the skin of the live tissue. However, it would be impossible to make proper diagnosis of the internal organs, such as the pancreas, which is located deep in the body of the human being. It is because the resolution of a tomographic image is lowered due to a greater distance between the probe and the pancreas. Ultrasonic diagnosis of the pancreas could not be properly made at the back of the human being in spite of the fact that the pancreas is located at a relatively small distance from the back, since the backbone is present between the back and the pancreas. Under these circumstances, a new method has been developed in which an ultrasonic probe is inserted through the mouth into the stomach so that ultrasonic diagnosis can be effected with the probe oriented towards the pancreas. In this case, however, it would be difficult to correctly orient the probe toward the pancreas. Since an ultrasonic wave is hard to propagate through the air, it is necessary that the probe be made in intimate contact with the wall of the stomach. However, the conventional method for ultrasonically diagnosing the pancreas with the probe oriented inside the stomach has not been reduced to practice, because the probe can hardly be made in intimate contact with the wall of the stomach, while being correctly oriented toward the pancreas.

SUMMARY OF THE INVENTION

It is accordingly the object of this invention to provide an endoscope which can accurately orient an ultrasonic wave toward a region of interest of a human being and can cause the ultrasonic wave radiating face of an ultrasonic probe to be brought into intimate contact with the internal wall corresponding to the region of interest so that a high-resolution tomographic image can be obtained and accurate diagnosis can be performed.

According to this invention there is provided an endoscope including a control section having an eyepiece section for viewing and an operating section for operating a bendable tube to permit it to be bent, a flexible tube connected at one end to the operating section, and a distal end section having a viewing window connected to one end of the bendable tube with the other end of the tube being connected to the other end of the flexible tube, in which at least one ultrasonic probe is provided at the distal end section with a vibration absorbing body attached thereto and has a directionality in a direction substantially the same as that of an optical axis of the viewing window provided in the distal end section in proximity to the ultrasonic probe.

BRIEF DESCRIPTION OF THE DRAWINGS

This invention will be described by way of example by referring to the accompanying drawings, in which.

DETAILED DESCRIPTION OF THE PREFERRED EMBODIMENTS

Figure 1:
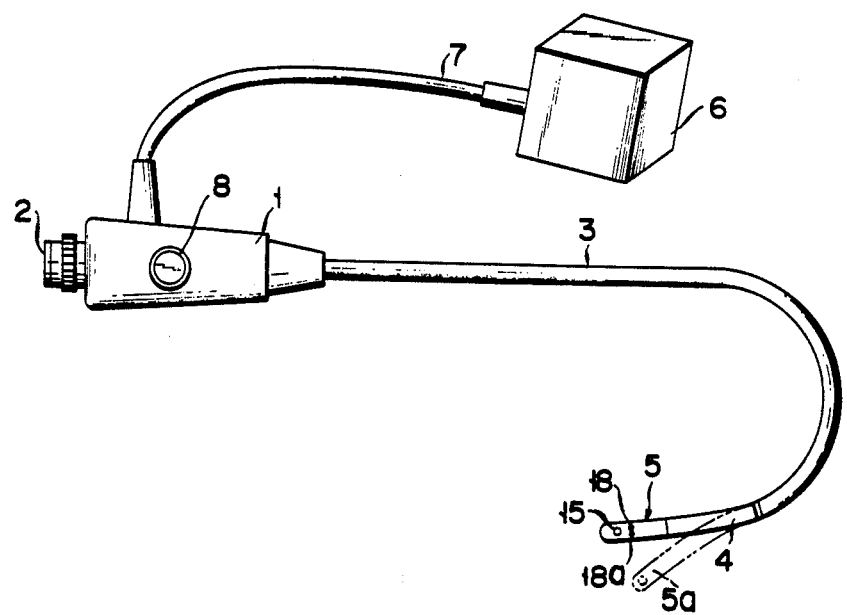
FIG. 1 is a view generally showing an endoscope according to one embodiment of this invention.

The embodiments of this invention will be described below by referring to the drawings. In these embodiments, like reference numerals are employed to designate like parts throughout the specification.

In FIG. 1 an eyepiece section 2 is provided at one end of a cylinder-like control section 1 and one end of a flexible tube 3 is connected to the other end of the control section 1 with the other end of the flexible tube 3 connected by a controllably bendable tube 4 to a cylinder-like distal end section 5. An image guide formed of optical fibers is inserted through the flexible tube 3. A universal cord 7 and operating knob 8 are projected from the side wall of the control section 1, the cord 7 being connected to a light source/electrical circuit section 6. A string means is inserted through the flexible tube 3. The string means is connected at its forward end to the rear end of the distal end section 5 through the bendable tube 4 and extends through the flexible tube 3 down to the control section 1. The rear end of the string means is connected to a control mechanism (not shown) which is located in the control section 1. The operating knob 8 is used to operate the control mechanism. The tube 4 can be controllably bent by operating the string means by the operating knob 8 so that the distal end section 5 can be bent to such a position as indicated by reference numeral 5a. As a mechanism for bending the bendable tube 4 by the operating knob 8 use may be made of one as set out in detail, for example, in U.S. Pat. No. 3,788,304 issued on Jan. 29, 1974.

The light source/electrical circuit section 6 includes a lamp as a light source. A light guide is inserted through the universal cord 7 and extends into the bendable tube 4 after passing through the flexible tube 3. Light from the light source is conducted through the light guide to the control section 1 and then through the flexible tube 3 and bendable tube 4 to an illumination window 18a where it is emitted to the outside. A viewing window 18 and ultrasonic probe 12 as will be later described are provided in the neighborhood of the illumination window 18a.

Figure 2:
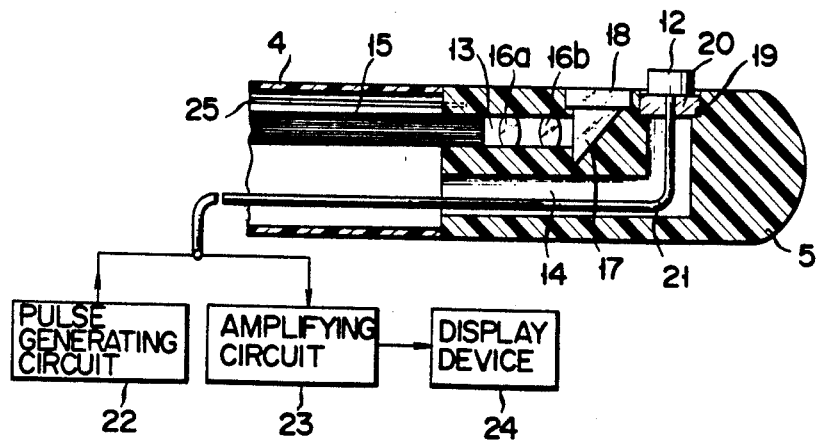
FIG. 2 is an enlarged, longitudinal sectional view showing a distal end section of the endoscope of FIG. 1.

The distal end section 5 is constructed as shown in FIG. 2. The forward open end of the bendable tube 4 is blocked by the distal end section 5 which is made of, for example, a rigid plastic. The forward end of the distal end section 5 is hemispherically formed and the rear end portion of the distal end section 5 has bores 13 and 14 which are formed along the longitudinal direction of the distal end section 5. An image guide 15 is connected at one end to the eyepiece 2 and the other end of the image guide 15 extends a predetermined distance into the bore 13 of the distal end section 5. A pair of objective lenses 16a, 16b are disposed in the bore 13 of the distal end section 5 in a manner to face the end of the image guide 15. The bore 13 is opened at the side wall of the distal end section 5 to permit an optical axis to be bent substantially at 90°. A prism 17 is provided in the neighborhood of the objective lens 16b to 90°-refract the optical axis of light which passes through the lenses 16a, 16b, the lens 16a being located remote from the end of the image guide 15. The open end of the bore 13 is closed by the above-mentioned viewing window 18 which is made of a transparent glass plate. The bore 14 is bent substantially at 90° within the distal end section 5 and communicates with a side opening 19 formed in proximity to the viewing window 18 and is provided between the viewing window 18 and the forward end of the distal end section 5. The side opening 19 is blocked by a damper 20 on which an ultrasonic probe 12 is disposed and bonded. At this state, the probe 12 is projected a predetermined distance from the outer wall of the distal end section 5. The probe 12 and damper 20 are usually manufactured and sold as a one-piece unit. The optical axis of the viewing window 18 is oriented in a direction substantially vertical to the longitudinal axis of the distal end section 5 and the probe 12 is arranged such that the direction of an ultrasonic wave from the probe 12 is substantially the same as that of the optical axis of the viewing window 18.

The probe 12 comprises, as will later be described, a couple of electrodes and a piezoelectric element sandwiched between these electrodes. A cable 21 is connected to the electrodes and extends through the damper 20. The cable 21 is connected to the light source/electrical circuit section 6 via the damper 20, bore 14 of the distal end section 5, bendable tube 4, flexible tube 3, control section 1 and universal cord 7.

As shown in FIG. 2 a pulse generating circuit 22, amplifying circuit 23 and display device 24 are arranged in the light source/electrical circuit section 6. The pulse generating circuit 22 delivers an excited pulse signal via the cable 21 to the probe 12 and the amplifying circuit 23 receives a signal corresponding to an ultrasonic wave echoed from a region of interest of a human being and amplifies it. The amplified signal is sent to a display device 24 using, for example, a cathode ray tube where a tomographic image is displayed. A method for energizing such an ultrasonic probe to permit an ultrasonic wave to be emitted and for receiving a signal echoed back from a region of interest and displaying it on the screen of a display device after being amplified is disclosed in detail, for example, in U.S. Pat. No. 3,404,560 issued on Oct. 8, 1968. In the embodiment of this invention use may be made of an ultrasonic testing system as set forth in U.S. Pat. No. 3,404,560. A string 25 is connected at one end to the mechanism adapted to be operated by the operating knob 8, and the other end of the string 25 is fixedly embedded into the rear end portion of the distal end section 5. A third bore, not shown, is provided in the distal end section 5 and extends along the bore 13. The forward open end of the third bore communicates with the illumination window 18a (FIG. 1) which is provided adjacent the viewing window 18. The light guide is passed through the third bore to permit light from the illumination lamp in the light source/electrical circuit section 6 to be conducted to the illumination window 18a.

Figure 3:
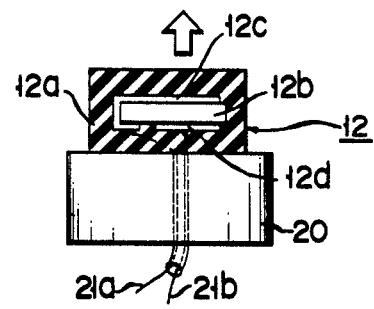
FIG. 3 is a cross-sectional view of an ultrasonic vibration member used for an ultrasonic probe.

The structure of the probe 12 will be explained below by reference to FIG. 3. In FIG. 3 the piezoelectric element 12b is encapsulated with an insulating layer 12a made of epoxy resin. The insulating layer 12a is formed on the upper surface of the damper 20 and is made of rubber, urethane and silicone resin. As the piezoelectric element 12b use may be made of, for example, lead zirconate titanate (PZT) or lithium niobate. The upper surface of the piezoelectric element 12b is covered by a first electrode 12c which is formed by, for example, evaporation. One end of the electrode 12c extends along one side of the piezoelectric element 12b and is bent into contact with part of the lower surface of the piezoelectric element 12b. A second electrode 12d is formed by evaporation on the lower surface of the piezoelectric element 12b such that it is spaced some distance apart from said one end of the electrode 12c. In this way, the piezoelectric element 12b is sandwiched by the electrodes 12c, 12d. Lead-in wires 21a and 21b are connected at one end to the electrodes 12c and 12d, respectively, and at the other end to the cable 21. When a pulse-like voltage is applied from the pulse generating circuit 22 between the electrodes 12c and 12d an ultrasonic wave generated from the piezoelectric element 12b is oriented in a direction indicated by an arrow in FIG. 3.

Figure 4:
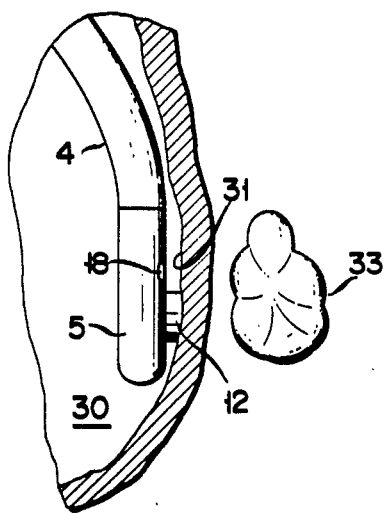
FIG. 4 is a view for explaining the state in which the pancreas of a human being is ultrasonically diagnosed at the side of the stomach wall using the embodiment shown in FIGS. 1 and 2.

The operation of the endoscope will be explained below in connection with FIGS. 1 to 3. Suppose that the diagnosis of the pancreas of FIG. 4 is effected using the embodiment of FIGS. 1 to 3. The distal end section 5 of the endoscope is inserted through the mouth into the stomach 30. When the distal end section 5 reaches the stomach 30 as shown in FIG. 4 the lamp in the light source/electrical circuit section 6 is lighted. Light is emitted through the illumination window 18a to permit the stomach wall 31 to be viewed through the eyepiece section 2. The viewing window 18 is oriented toward the stomach wall portion 31 corresponding to a pancreas 33, while observing the stomach 30 through the viewing window 18. As a result, the probe 12 is correctly oriented toward the pancreas 33. In this state, the tube 4 is bent by operating the operation knob 8 so that the viewing window 18 is pushed toward the stomach wall portion 31 with the probe in intimate contact with the stomach wall portion 31. When in this state a pulse signal of a frequency of, for example, 5 to 15 MHz from the circuit 22 is applied to the probe 12, the probe 12 is excited to produce a pulse-like ultrasonic wave. The ultrasonic wave is correctly propagated toward the pancreas 33 through the stomach wall portion 31. Since the stomach wall 31 and pancreas 33 have a different acoustic impedance, an echo signal is produced from a boundary between the stomach wall 31 and the pancreas 33. The echo signal is reflected back into the probe 12 where it is transduced into an electrical signal.

The signal is amplified by the amplifying circuit 23 and displayed, as a tomographic image corresponding to the pancreas 33, on the screen of the display device 24. As a result, the operator or doctor can correctly judge the presence, or the location, of any affected portion such as cancer of the pancreas 33.

Figure 5:
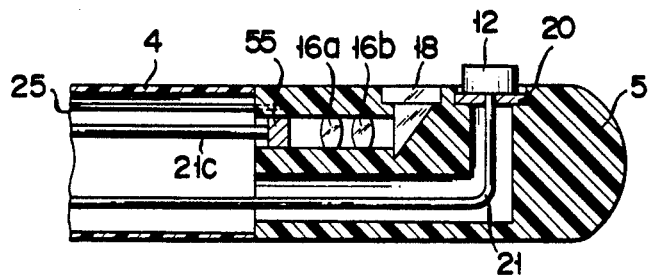
FIG. 5 is a longitudinal cross-sectional view showing a modified form of endoscope of this invention shown in FIG. 2.

FIG. 5 shows a modified form of endoscope of this invention. In this modification, a solid-state image pickup device 55 using a charge coupled device (CCD) is employed in place of the image guide 15 of FIG. 2. An image signal obtained at the solid-state image pickup device 55 is supplied through a cord 21c to a monitor using a television display device and the optical image obtained through the viewing window 18 is displayed on the screen of the monitor, making it unnecessary for an operator to observe the body part of a human being directly through the eyepiece 2 of FIG. 1. As the operator can operate the endoscope while amplifying an image on the screen of the display device as required, the probe 12 can be oriented more accurately toward the region of interest.

Figure 6:
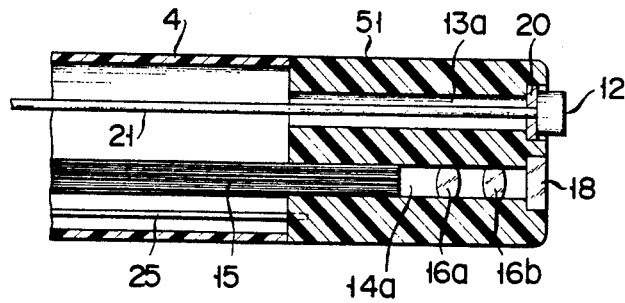
FIGS. 6, 7 and 8 are longitudinal cross-sectional views each showing a different embodiment of this invention.

In an embodiment as shown in FIG. 6, bores 13a, 14a are formed along the longitudinal direction of a cylindrical distal end section 51. A cord 21 is inserted through the bore 13a and then through a damper 20 and connected to a couple of electrodes of an ultrasonic probe 12. The damper 20 is disposed in a recess formed at the front opening of the bore 13a. The bore 14a is located adjacent the bore 13a and has a recess at the front side of the distal end section 51. A viewing window 18 is disposed in the front recess of the bore 14a. The probe 12 is projected from the front end face of the distal end section 51. The probe 12 can be correctly oriented toward a region of interest by operating the knob 8 (FIG. 1) such that the viewing window 18 is pushed toward the region. The endoscopes of FIGS. 2 and 6 may be selectively used, as required, according to which internal part or organ is observed for diagnosis.

Figure 7:
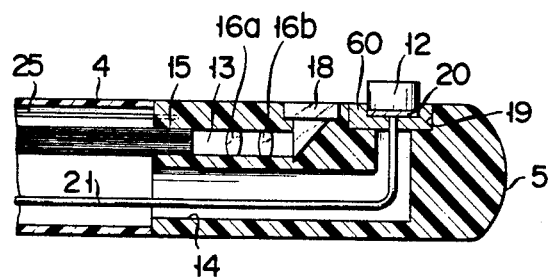

In the embodiment of FIG. 7 a unitary body of a damper 20 and probe 12 as shown in FIG. 2 is partially embedded in an elastic body 60 which in turn is fitted in a recess formed in the side wall of a distal end section 5. The elastic body 60 is made of rubber, urethane or silicone resin. The recess communicates with a bore 14 formed in the distal end section 5. The elastic body 60 serves as an elasticity-matching member for matching the elasticity between the damper 20 and the distal end section 5.

Figure 8:
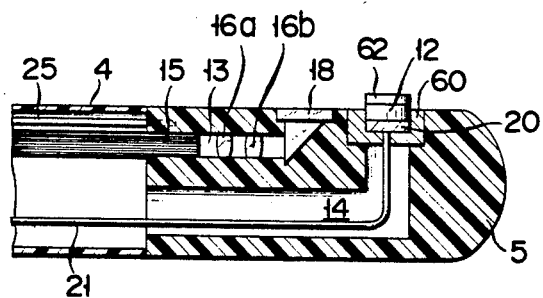

In an embodiment shown in FIG. 8, a porous elastic body 62 made of, for example, urethane or silicone resin is bonded to the surface of the probe 12 such that it is projected from the side wall of the distal end section 5. The remaining structure of the embodiment of FIG. 8 is the same as that of the embodiment of FIG. 7. If water is kept absorbed in the porous elastic body 62 the elastic body 62 serves as a good conductor for the ultrasonic wave and there is no possibility that the detection sensitivity will be lowered. In the embodiment of FIG. 8 no pain or damage will be imparted to the patient even if the elastic body 62 is strongly pushed into the internal wall of the body cavity.

What is claimed is:

1. An endoscope comprising a control section having an eyepiece section for observation and an operating section, a flexible tube connected at one end to the operating section, a bendable section connected at one end to the other end of the flexible tube, a distal end section provided at the other end of the bendable section, and bending means for bending said bendable section by the operating section, the bending means comprising at least one string member connected at one end to the operating section and fixed at the other end to the distal end section, said distal end section having a viewing window, in which at least one ultrasonic probe is provided at the distal end section, said probe having a vibration absorbing body attached thereto and a directionality in a direction substantially the same as that of an optical axis of the viewing window provided in the distal end section, said ultrasonic probe having an ultrasonic wave radiating and receiving surface which is projected from the surface of the distal end section and an ultrasonic wave conducting element formed of a soft, porous, water absorbing elastic body which is bonded to the surface of said ultrasonic probe, and said ultrasonic probe is provided in juxtaposition with the viewing window.

2. An endoscope according to claim 1 in which said ultrasonic probe and the viewing window are provided at the longitudinal side surface of said distal end section.

3. An endoscope according to claim 1 in which said distal end section is cylindrical in configuration and said ultrasonic probe is provided at the far end face of said distal end section such that it is located in proximity to the viewing window.

4. An endoscope according to claim 1 in which said ultrasonic probe is electrically connected to an external circuit by a cord which is inserted through the distal end section, flexible tube and control section, said external circuit comprising a pulse generating circuit for generating a pulse-like voltage for supply to the probe, an amplifying circuit for amplifying a signal which is produced at the probe according to an echoed ultrasonic wave, and a display device for displaying a tomographic image corresponding to a region of interest which is obtained by the output of said amplifying circuit.

5. An endoscope according to claim 1 in which the viewing window is included as one of a viewing optical system provided over the distal end section and flexible tube, said viewing optical system including a solid-state image pickup element for converting an optical image received from the viewing window to an electrical signal.

6. An endoscope comprising a control section having an eyepiece section for observation and an operating section, a flexible tube connected at one end to the operating section, a bendable section connected at one end to the other end of the flexible tube, a distal end section provided at the other end of the bendable section, and bending means for bending said bendable section by the operating section, the bending means comprising at least one string member connected at one end to the operating section and fixed at the other end to the distal end section, said distal end section having an outer surface and a viewing window, at least one ultrasonic probe mounted on the outside surface of the distal end section, said probe having a vibration absorbing body attached thereto and a directionality in a direction substantially the same as that of an optical axis of the viewing window provided in the distal end section, said ultrasonic probe having an ultrasonic wave radiating and receiving surface which is spaced from the outer surface of the distal end section so the probe projects outwardly of the distal end section so that the ultrasonic wave radiating surface can be brought into intimate contact with an internal body wall corresponding to a region of interest so that high-resolution tomographic images can be obtained, and an ultrasonic wave conducting element formed of a soft, porous, water absorbing elastic body which is bonded to the surface of said ultrasonic probe, said ultrasonic probe being located in close juxtaposition with the viewing window so that extremely accurate positioning of the probe can be made.

* * * * *